United States Patent [19]
Baron et al.

[11] 4,306,055
[45] Dec. 15, 1981

[54] POLYCARBONATES HAVING SULFUR-CONTAINING PHENOLIC DIOLS INCORPORATED THEREIN

[75] Inventors: Arthur L. Baron; Sivaram Krishnan, both of New Martinsville, W. Va.; Joseph R. Thomas, Belmont, Calif.

[73] Assignee: Mobay Chemical Corporation, Pittsburgh, Pa.

[21] Appl. No.: 157,603

[22] Filed: Jun. 9, 1980

Related U.S. Application Data

[63] Continuation-in-part of Ser. No. 65,787, Aug. 13, 1979, abandoned.

[51] Int. Cl.³ .................. C07C 147/10; C08G 75/20
[52] U.S. Cl. .................................. 528/171; 528/174; 568/33; 568/35
[58] Field of Search .................. 528/171, 174; 568/33, 568/35

[56] References Cited
U.S. PATENT DOCUMENTS 3,269,986  8/1966  Goldberg ........................ 528/171
3,419,526  12/1968 Schnell et al. .................. 528/174
3,729,447  4/1973  Haberland et al. ............. 528/174
3,770,832  11/1973 Leslie et al. ...................... 568/33
3,809,682  5/1974  Studinka et al. ................ 528/174
3,912,688  10/1975 Schiller et al. .................. 528/174
4,043,980  8/1977  Baron et al. ..................... 528/174

FOREIGN PATENT DOCUMENTS 53-95545  1/1978  Japan .
53-40693  9/1978  Japan .

OTHER PUBLICATIONS

Fuson, Reactions of Organic Compounds, John Wiley, New York, (1962), pp. 40-41.
Norman, Principles of Organic Synthesis, Methuen, London, (1968), p. 356.
Noller, Chemistry of Organic Compounds, Saunders, Philadelphia, (1965).
Glutz, Annalen, vol. 147, Mar. 5, 1980, pp. 52-66.

Primary Examiner—H. S. Cockeram
Attorney, Agent, or Firm—Gene Harsh; Lawrence S. Pope; Aron Preis

[57] ABSTRACT

Polycarbonate resins are based upon the reaction of an aromatic diol and a carbonic acid derivative. A sulfur containing difunctional phenolic compound represented by the structural formula:

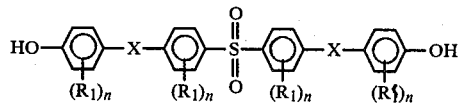

wherein $R_1$ is a lower alkyl having 1 to 4 carbon atoms and "n" equals 0 to 4 and X is S or $SO_2$ either totally or partially substitutes for said aromatic diol. Polycarbonates prepared in accordance with the invention exhibit good heat distortion characteristics and long term aging properties.

11 Claims, No Drawings

POLYCARBONATES HAVING SULFUR-CONTAINING PHENOLIC DIOLS INCORPORATED THEREIN

This application is a continuation-in-part of our co-pending application Ser. No. 65,787 filed Aug. 13, 1979, now abandoned.

BACKGROUND OF THE INVENTION

1. Field of the Invention

This invention relates to polycarbonate resins and more particularly to polycarbonate resins based on sulfur containing phenolic compounds.

2. Description of the Prior Art

Polycarbonates derived from reactions involving dihydroxy compounds and carbonic acid derivatives have found extensive commercial application because of their excellent mechanical and physical properties. These thermoplastic polymers are particularly suited for the manufacture of molded article products requiring impact strength, rigidity, toughness, thermal and dimensional stability as well as excellent electrical properties.

When a polycarbonate article is to be used in above ambient temperature environments, it is necessary that the polycarbonate be adapted to have proper physical properties at these temperatures. For example, polycarbonates have found extensive use in automotive applications due to their light weight in relation to their strength characteristics. When a polycarbonate is used in such applications, it must retain its dimensional stability during manufacture of the automobile. Particularly, the polycarbonate must retain its dimensional stability in a paint oven or during similar high temperature processing of the vehicle.

Further, polycarbonates have been found useful in the appliance industry, for example in industrial power tool housings and similar applications where the tool and, hence the polycarbonate, are required to withstand continuous use at elevated temperatures.

Further, in some applications polycarbonates are required to be subjected to increased temperatures over their entire service life and, further, in high humidity environments.

Accordingly, in order to provide this dimensional stability at elevated temperatures and in humid atmospheres, in accordance with the present invention, a polycarbonate is provided which has improved dimensional stability at elevated temperatures and after aging at high temperature and humidity.

BRIEF DESCRIPTION OF THE INVENTION

Polycarbonate resins are based upon the reaction of an aromatic diol and a carbonic acid derivative. A sulfur containing difunctional phenolic compound represented by the structural formula:

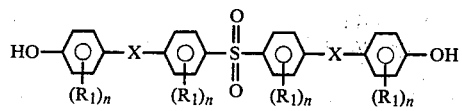

wherein $R_1$ is a lower alkyl having 1 to 4 carbon atoms, "n" equals 0 to 4 and X is S or $SO_2$, completely or partially replaces the aromatic diols of said reaction. Polycarbonates prepared in accordance with the invention exhibit good heat distortion characteristics and long term aging properties.

DETAILED DESCRIPTION OF THE INVENTION

When used herein "copolycarbonate resin" means the neat resin without additives; "polycarbonate" means the polycarbonate resin or copolycarbonate resin, with additives therein. "Aromatic diol" means an aromatic diol having no sulfur therein and primarily having only carbon hydrogen and oxygen atoms and which may have halogen atoms. "Aromatic dihydroxy compound" means any or all compounds which are aromatic diols, halogenated aromatic diols or sulfur containing difunctional phenolic compounds.

The polycarbonate resins of the invention may be prepared by conventional methods of preparation for polycarbonate resins and may have a weight average molecular weight of 10,000 to 200,000 and preferably a melt flow rate of 1 to 24 gram/10 min. at ASTM D 1238 Condition O.

Any suitable processes, reactants, catalysts, solvents, conditions and the like for the production of the copolycarbonate resins of this invention which are customarily employed in polycarbonate resin syntheses may be used such as disclosed in German Pat. Nos. 1,046,311 and 962,274 and U.S. Pat. Nos. 3,248,414; 3,153,008; 3,215,668; 3,187,065; 3,028,365; 2,999,846; 2,964,974; 2,970,137; 2,991,273 and 2,999,835, all incorporated herein by reference. The preferred process is the interfacial polycondensation process.

According to the interfacial polycondensation process copolycarbonate resins are obtained by reacting the aromatic dihydroxy compounds with an alkali metal hydroxide or alkaline earth metal oxide or hydroxide to form the salt of the hydroxy compounds. The salt mixture is present in an aqueous solution or suspension and is reacted with phosgene, carbonyl bromide, bischloroformic esters of the aromatic dihydroxy compounds. An organic solvent is provided in the reaction admixture which is a solvent for the polymer but not for the aromatic dihydroxy salts. Thus, chlorinated aliphatic hydrocarbons or chlorinated aromatic hydrocarbons are used as the organic solvent which dissolves the condensation product. In order to limit the molecular weight, one may use monofunctional reactants such as monophenols, for example the propyl-, isopropyl- and butyl-phenols, especially p-tert.-butyl-phenol and phenol itself. In order to accelerate the reaction, catalysts such as tertiary amines, quaternary ammonium, phosphonium or arsonium salts and the like may be used. The reaction temperature should be about $-20°$ to $+150°$ C., preferably 0° C. to about 100° C.

According to the polycondensation process in a homogeneous phase, the dissolved reaction components are polycondensed in an inert solvent in the presence of an equivalent amount of a tertiary amine base required for: absorption of the generated HCl, such as e.g. N,N-dimethyl-aniline, N,N-dimethyl-cyclohexylamine or preferably, pyridine and the like. In still another process, a diaryl carbonate can be transesterified with the aromatic dihydroxy compounds to form the polycarbonate resin.

It is to be understood that it is possible to combine in the processes described above in a chemically meaningful way the aromatic dihydroxy compounds, monohydroxy compounds in the form of the alkali metal salts and/or bis-haloformic acid esters, and the amount of phosgene or carbonyl bromide then still required in order to obtain high molecular products. Other methods of synthesis in forming the polycarbonates of the invention such as disclosed in U.S. Pat. No. 3,912,688, incorporated herein by reference, may be used.

Suitable aromatic diphenols are, for example, (4,4'-dihydroxy-diphenyl)-methane, 2,2'-(4,4'-dihydroxy-diphenyl)-propane, 1,1-(4,4'-dihydroxy-diphenyl)-cyclohexane, 1,1-(4,4'-dihydroxy, 3,3'-dimethyl-diphenyl)-cyclohexane, 1,1-(2,2'-dihydroxy-4,4'-dimethyl-diphenyl)-butane, 2,2-(2,2'-dihydroxy-4,4'-di-tert.-butyl-diphenyl)-propane or 1,1'-(4,4'-dihydroxy-diphenyl-1-phenylethane, furthermore, methane derivatives which carry besides two hydroxyaryl groups an alkyl residue with at least two carbon atoms and a second alkyl residue with one or more carbon atoms, such as 2,2-(4,4'-dihydroxy-diphenyl)-butane, 2,2-(4,4'-dihydroxy-diphenyl)-pentane, 3,3-(4,4'-dihydroxy-diphenyl)-pentane, 2,2-(4,4'-dihydroxy-diphenyl)-hexane, 3,3-(4,4'-dihydroxy-diphenyl)-hexane, 2,2-(4,4'-dihydroxy-diphenyl)-4-methylpentane, 2,2-(4,4'-dihydroxy-diphenyl)-heptane, 4,4-(4,4'-dihydroxy-diphenyl)-heptane (melting point 148°–149° C.) or 2,2-(4,4'-dihydroxy-diphenyl)-tri-decane. Suitable di-(monohydroxyaryl)-alkanes, the two aryl residues of which are different are, for example, 2,2-(4,4'-dihydroxy-3'-methyl-diphenyl)-propane and 2,2-(4,4'-dihydroxy-3-methyl-3'-isopropyl-diphenyl)-butane. Suitable di-(monohydroxyaryl)-alkanes, the alkyl residue of which, linking the two benzene rings, is substituted by an aryl residue are for instance (4,4'-dihydroxy-diphenyl)-phenyl-methane and 1,1-(4,4'-dihydroxy-diphenyl)-1-phenyl-ethane.

Suitable dihydroxybenzenes and substituted dihydroxybenzene are hydroquinone, resorcinol, pyrocatecol, methyl hydroquinone and the like. Other suitable dihydroxy-aromatic compounds are 4,4'-dihydroxy-diphenylene, 2,2'-dihydroxy-diphenylene, dihydroxynaphthalene and dihydroxyanthracene.

Halogenated phenolic diols are typically any suitable bis-hydroxyaryl components such as, for example, the halogen containing bisphenols such as 2,2-(3,3,3',5'-tetrachloro-4,4'-dihydroxy-diphenyl)-propane; 2,2-(3,5,3',5'-tetrabromo-4,4'-dihydroxy-diphenyl)-propane; 2,2-(3,3-dichloro-4,4'-dihydroxy-diphenyl)-propane; 2,2-(3,5-dichloro-4,4'-dihydroxy-diphenyl)-propane; 2,2-(3,3'-dichloro-5,5'-dimethyl-4,4'-dihydroxy-diphenyl)-propane; 2,2-(3,3'-dibromo-4,4'-dihydroxy-diphenyl)-propane and the like and are represented by the structural formula:

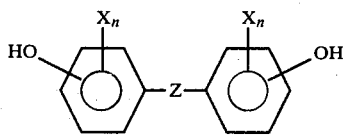

wherein Z is methylene or isopropylidine and X is halogen, preferably chlorine or bromine and most preferably bromine and n is 1 to 4.

These halogenated diols are incorporated into the polycarbonate at levels sufficient to impart flame retardant characteristics. For example, a halogen content of about 3 to 10 percent by weight is normally sufficient.

The sulfur containing difunctional phenolic compounds useful in the practice of the invention are represented by the structural formula:

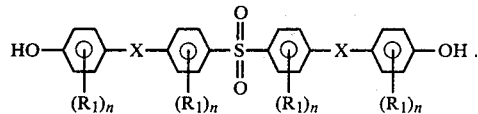

Two particularly useful sulfur containing difunctional phenolic compounds are: 4,4'-bis(p-hydroxyphenylthio)-phenylsulfone, represented by the structural formula:

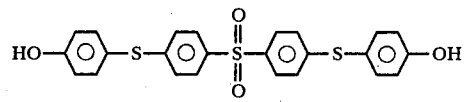

and 4,4'-bis(p-hydroxyphenylsulfonyl)-phenylsulfone, represented by the structural formula:

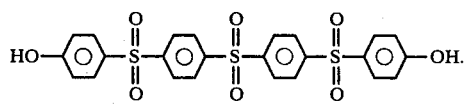

Either compound can, according to the practice of the invention, be reacted with carbonic acid derivatives, to yield useful resins.

Preferably, the sulfur containing difunctional phenolic compound is incorporated into the polycarbonate in partial substitution of the aromatic diol used for the preparation of the polycarbonate, particularly preferred levels being up to 20 wt. % of said compound, especially to 10 wt. %.

Most preferably, the 4,4'-bis(p-hydroxyphenylsulfonyl)-phenylsulfone is incorporated into the polycarbonate at a level of between about 5 to 20 percent by weight based on the total weight of aromatic dihydroxy compound reacted with the carbonic acid ester derivative. The 4,4'-bis(p-hydroxyphenylthio)-phenylsulfone is preferably incorporated at a level of up to about 20 percent by weight and more preferably up to about 10 percent by weight based on the total weight of aromatic dihydroxy compound reacted with the carbonic acid ester derivative.

The invention will be further illustrated by the following Examples.

EXAMPLES

Example 1

4,4'-bis(p-hydroxyphenylthio)-phenylsulfone is prepared as follows:

To a 12 liter reactor equipped with a stirrer and dried in a nitrogen atmosphere was charged 1,260 g (10 mols) of 4-mercaptophenol and 500 ml of dimethylformamide. The mercaptophenol/dimethylformamide solution was heated to 60° C. 1,450 g (10.5 mols) of K₂CO₃ was charged to the dimethylformamide mercaptophenol solution with agitation. The solution was then heated to 100° C. and held at 100° C. for 2¾ hours. A solution of 1,436 g (5 mols) of 4,4'-dichlorodiphenylsulfone and 3,250 ml dimethylformamide was prepared and heated to about 50° C. to provide a homogeneous solution. The chlorophenyl sulfone solution was added by a dropping funnel to the reactor over a period of 30 minutes allowing the temperature within the reactor to rise to 110° C. The temperature was held at 110°–115° C. for 20 hours subsequent to the addition of the chlorophenyl sulfone solution.

The crude reaction product was filtered to remove the K₂CO₃. The K₂CO₃ was washed with 1½ liters of dimethylformamide at 60°–110° C. The filtrate was precipitated by its addition to a 37 percent by weight solution of HCl. The precipitant and the aqueous acid DMF supernatant was cooled at room temperature and the aqueous phase was decanted. The precipitate was washed twice in boiling water to remove residual hydrochloric acid and dimethylformamide. The crude, relatively dry 4,4'-bis(p-hydroxyphenylthio)-phenylsulfone was dissolved in MCB (monochlorobenzene) and methanol and heated to 90° C. The mixture was then cooled to 25° C. to crystallize the 4,4'-bis(p-hydroxyphenylthio)-phenylsulfone. The crystallized reaction product was filtered and washed with cold (less than 30° C.) monochlorobenzene (MCB). The crystallized product was dried in a vacuum oven which temperature was increased from room temperature to 120° C. over a six-hour period to remove most of the MCB. The vacuum oven was held at 120° C. overnight to completely dry the product. The product has a melting point of 183°–184° C.

Example 2

4,4'-bis(p-hydroxyphenylsulfonyl)-phenylsulfone was prepared as follows:

To an agitated flask under a nitrogen atmosphere was charged 4,000 ml of acetic anhydride and 1,500 ml of distilled water. The mixture was heated to 35° C. and 400 g (0.86 mols) of 4,4'-bis(p-hydroxyphenylthio)-phenylsulfone prepared in accordance with Example 1 was added slowly. The reaction mixture was then heated to 80°–85° C. until a homogeneous solution was formed. Eight pints of 30 percent hydrogen peroxide (13 mols) were then added slowly over about ½ hour time period. After the peroxide was added, the solution was heated to reflux (102°–103° C.) for two hours and cooled slowly to 25° C. 1,500 ml distilled water was added to this slurry and the slurry was filtered. The white solid was washed twice with distilled water and once with methanol and vacuum dried at 100° C. The product recovered had a melting point of 295°–296° C.

Example 3

An aqueous solution was prepared by simultaneously charging to a suitable premix vessel with agitation 67.6 kg of water, 13.29 kg of bisphenol A, 0.27 kg of 4,4'-bis(p-hydroxyphenylthio)-phenylsulfone prepared in accordance with Example 1, 9.7 kg of 50 percent aqueous sodium hydroxide solution and 0.30 kg of tert.-butylphenol. 33.75 kg per hour of the above solution was continuously phosgenated with 2.87 kg of phosgene per hour in 50.38 kg of 1:1 methylene chloride:chlorobenzene solvent. 2.5 kg/hour of 25 percent aqueous sodium hydroxide solution was continuously added to the reaction mixture to provide the proper basicity for the interfacial polycondensation. The precondensate as obtained above was then mixed with a solution/hour of 25 g of triethylamine and 2.8 kg of 25 percent aqueous sodium hydroxide solution and was further reacted in a stirred kettle cascade over the course of an average dwell time of 30 minutes. The organic phase was separated from the aqueous phase and the organic phase was washed with 1 percent aqueous sodium hydroxide solution, separated and then the organic phase was washed with 1 percent aqueous phosphoric acid solution and separated. The organic phase was simultaneously washed and separated three times with water. The polymer was recovered from the organic phase by concentrating the polymer by solvent evaporation and subsequently passing the polymer through a devolatilizing extruder. The polymer as above prepared had 1.7 percent by weight of 4,4'-bis(p-hydroxyphenylthio)-phenylsulfone based on the weight of total dihydroxy phenolic compound incorporated into the polycarbonate. The polymer was pelletized and tested for physical, optical and rheological properties. The test results are reported on Table I along with the test results of the following examples.

Examples 4 and 5

Example 3 was repeated except that the stoichiometric amounts of bisphenol A and 4,4'-bis(p-hydroxyphenylthio)-phenylsulfone were varied. Table I shows the weight percent of the constituents.

Examples 6 and 7

The procedure of Example 3 was repeated except that varying concentrations of 4,4'-bis(p-hydroxyphenylsulfonyl)-phenylsulfone were substituted for the 4,4'-bis(p-hydroxyphenylthio)-phenylsulfone. Table I shows the weight percent of the constituents along with the physical, optical and rheological properties of polycarbonates prepared using these polycarbonate resins.

Examples 8 and 9

The copolycarbonate prepared in Example 5 having therein 20 percent by weight of 4,4'-bis(p-hydroxyphenylthio)-phenylsulfone based on the weight of bisphenol A used, was let down with bisphenol A homopolycarbonate having a melt flow of 7.8 g/10 min. to provide a polycarbonate having 10 percent in Example 8, and 5 percent in Example 9 of the polymerized 4,4'-bis(p-hydroxyphenylthio)-phenylsulfone based on the bisphenol A incorporated into the polycarbonate. The polycarbonates of Examples 8 and 9 were tested for physical, optical and rheological properties. The test results are reported on Table I.

TABLE I

| EXAMPLE | 3 | 4 | 5 | 6 | 7 | 8 | 9 | Control[2] |
|---|---|---|---|---|---|---|---|---|
| % 4,4'-bis(p-hydroxyphenylthio)-phenylsulfone[1] | 1.7 | 5 | 20 | | | 10 | 5 | 0 |
| % 4,4'-bis(p-hydroxyphenylsulfonyl)-sulfone[1] | | | | 1.7 | 5 | | | 0 |
| Melt flow g/10 min. (ASTM) D-1238, Condition 0 | 4.8 | 6.0 | 8.4 | 16.5 | 21.1 | 8.2 | 8.5 | 7.8 |
| Melt stability at 300° C. Melt viscosity in k-Pa-S | | | | | | | | |
| 5 minutes | 0.66 | 0.49 | 0.37 | 0.19 | 0.19 | 0.38 | 0.41 | |
| 35 minutes | 0.76 | 0.59 | 0.32 | 0.21 | 0.19 | 0.46 | 0.41 | |
| 65 minutes | 0.74 | 0.56 | 0.38 | 0.20 | 0.19 | 0.46 | 0.41 | |
| Heat distortion temperature at 1.8kPa, °C. | 139 | 139 | 139 | 134 | 128 | 134 | 141 | 133 |
| Impact pproperties, Izod notched[3] J/m | | | | | | | | |
| Initial | 876 | 833 | 651 | 737 | 710 | 780 | 817 | 780 |

TABLE I-continued

| EXAMPLE | 3 | 4 | 5 | 6 | 7 | 8 | 9 | Control[2] |
|---|---|---|---|---|---|---|---|---|
| Oven aged at 110° C. | | | | | | | | |
| 3 days | | | 107 | | 112 | 117 | 123 | |
| 6 days | | | 101 | | 96 | 117 | 123 | |
| Aged in water at 82.2° C. | | | | | | | | |
| 1 day | | | 191 | | 176 | 96 | 96 | |
| Critical thickness (mils) | 228 | 209 | 160 | 168 | 162 | 158 | 184 | 184 |
| (4 mm) | 5.79 | 5.31 | 4.06 | 4.27 | 4.11 | 4.01 | 4.67 | 4.6 |

[1] Percentage based on total bisphenols incorporated into the polycarbonate.
[2] The control is a bisphenol A homopolycarbonate.
[3] Sample thickness of 3.2 millimeters, ASTM D-256.
[4] Mobay's method.

Thus, as is illustrated by the Examples and the test results shown in Table I, stable polycarbonates can be prepared using sulfur containing difunctional phenolic compounds as previously defined.

The copolycarbonates having up to 5 percent by weight of the 4,4'-bis(p-hydroxyphenylthio)-phenylsulfone exhibit high melt flow rates and increased impact properties over homopolycarbonates of bisphenol A. Further, polycarbonates prepared from blends of copolycarbonates having 4,4'-bis(p-hydroxyphenylthio)-phenylsulfone and homopolymers of bisphenol A exhibit increased or at least equal impact properties over the homopolycarbonate of bisphenol A.

The polycarbonates prepared from 4,4'-bis(p-hydroxyphenylsulfonyl)-phenylsulfone exhibit good impact properties at high melt flow rates along with good heat distortion temperatures.

All of the polycarbonates prepared and tested containing the sulfur containing difunctional phenolic compounds exhibit acceptable physical and rheological properties. Further, these polycarbonates are stable at molding temperatures and upon aging at elevated temperatures and in humidity. Therefore, it is clear that these polycarbonates will be readily applicable for a wide variety of the uses to which thermoplastic resins are put including injection molding and extrusion.

Although the invention has been described by specific Examples and with reference to specific methods of preparation it is only to be limited so far as is set forth in the accompanying claims.

What is claimed is:

1. A monomer of the structural formula

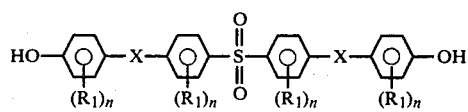

wherein $R_1$ is a lower alkyl having 1 to 4 carbon atoms, n is an integer from 0 to 4 and x is uniformly either S or $SO_2$.

2. A monomer, 4,4'-bis(p-hydroxyphenylthio)-phenylsulfone of the structural formula

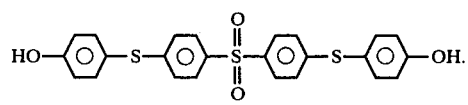

3. A monomer, 4,4'-bis(p-hydroxyphenylsulfonyl)-phenylsulfone of the structural formula

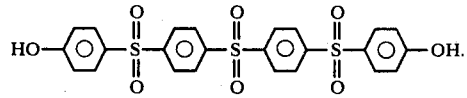

4. A thermoplastic aromatic polycarbonate comprising the reaction product of
(i) a monomer of the structural formula

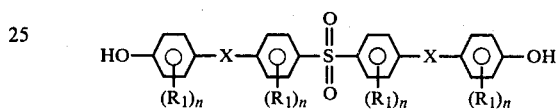

wherein
$R_1$ is a lower alkyl having 1 to 4 carbon atoms,
n is an integer from 0 to 4, and
X is uniformly either S or $SO_2$
(ii) a carbonic acid derivative and optionally,
(iii) an aromatic diol.

5. A thermoplastic aromatic polycarbonate of claim 4 wherein said monomer is of the structural formula

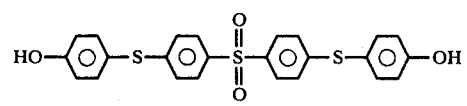

6. A thermoplastic aromatic polycarbonate of claim 4 wherein said monomer is of the structural formula

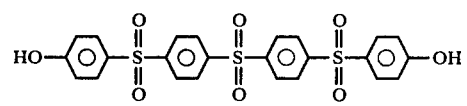

7. A thermoplastic aromatic polycarbonate of claim 4 wherein said carbonic acid derivative is selected from a group consisting of carbonyl bromide, phosgene, bis-chloroformic esters of said monomer or of an aromatic diol.

8. The method of preparing a thermoplastic aromatic polycarbonate comprising reacting
(i) a monomer of the structural formula

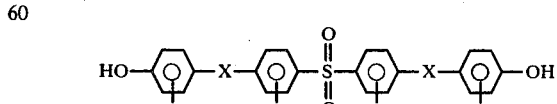

wherein
R is a lower alkyl having 1 to 4 carbon atoms,
n is an integer 0 to 4 and is uniformly either S or

with
(ii) a member selected from the group consisting of a carbonyl bromide, phosgene, a bis-chloroformic ester of (i) or of an aromatic diol, with optionally
(iii) an aromatic diol.

9. The method of claim 8 wherein said (iii) is 4,4'-dihydroxydiphenyl propane.

10. The method of claim 8 wherein said monomer is represented by the structural formula

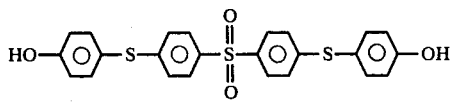

11. The method of claim 8 wherein said monomer is represented by the structural formula

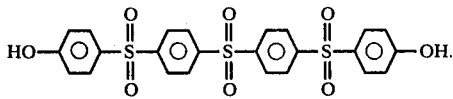

* * * * *